United States Patent
McGrath et al.

(10) Patent No.: US 7,367,673 B2
(45) Date of Patent: May 6, 2008

(54) METHOD AND APPARATUS FOR THE DIAGNOSIS OF GLAUCOMA AND OTHER VISUAL DISORDERS

(76) Inventors: John Andrew Murray McGrath, 4 Randolph Cliff, Edinburgh (GB) EH3 7TZ; John Scott Strachan, 6 Marchall Crescent, Edinburgh (GB) EH16 5HN (*) Notice: Subject to any disclaimer, the term of this patent is extended or adjusted under 35 U.S.C. 154(b) by 199 days.

(21) Appl. No.: 10/553,859

(22) PCT Filed: Apr. 21, 2004

(86) PCT No.: PCT/GB2004/001700

§ 371 (c)(1),
(2), (4) Date: Dec. 6, 2005

(87) PCT Pub. No.: WO2004/093668

PCT Pub. Date: Nov. 4, 2004

(65) Prior Publication Data

US 2006/0114414 A1    Jun. 1, 2006

(30) Foreign Application Priority Data

Apr. 22, 2003  (GB) .................................. 0309025.5

(51) Int. Cl.
*A61B 3/14* (2006.01)

(52) U.S. Cl. ....................... 351/209; 351/205; 351/206; 351/210; 351/211

(58) Field of Classification Search ................ 351/246, 351/209–211, 205–206
See application file for complete search history.

(56) References Cited

U.S. PATENT DOCUMENTS

| 5,422,690 | A | | 6/1995 | Rothberg et al. ........... 351/209 |
| 5,920,375 | A | * | 7/1999 | Fahle et al. ................. 351/246 |
| 6,089,714 | A | | 7/2000 | Galiana et al. ............. 351/202 |
| 6,367,932 | B1 | * | 4/2002 | Donaldson ................... 351/237 |

* cited by examiner

*Primary Examiner*—Scott J. Sugarman
*Assistant Examiner*—James R Greece
(74) *Attorney, Agent, or Firm*—Drinker Biddle & Reath LLP

(57) ABSTRACT

A subject (12) observes an image on a display (10). A control (18) produces a fixation image at a selected position in the display, followed by a stimulus spaced from the fixation image. An eye position sensor (14) detects a saccade movement towards the stimulus. The stimulus is then replaced with a fixation image and the cycle repeated. The time taken to saccade plus the intensity of the stimulus are used to produce a retinal map of field of vision, or to assess other characteristics of the subject.

41 Claims, 2 Drawing Sheets

METHOD AND APPARATUS FOR THE DIAGNOSIS OF GLAUCOMA AND OTHER VISUAL DISORDERS

Figure 1:
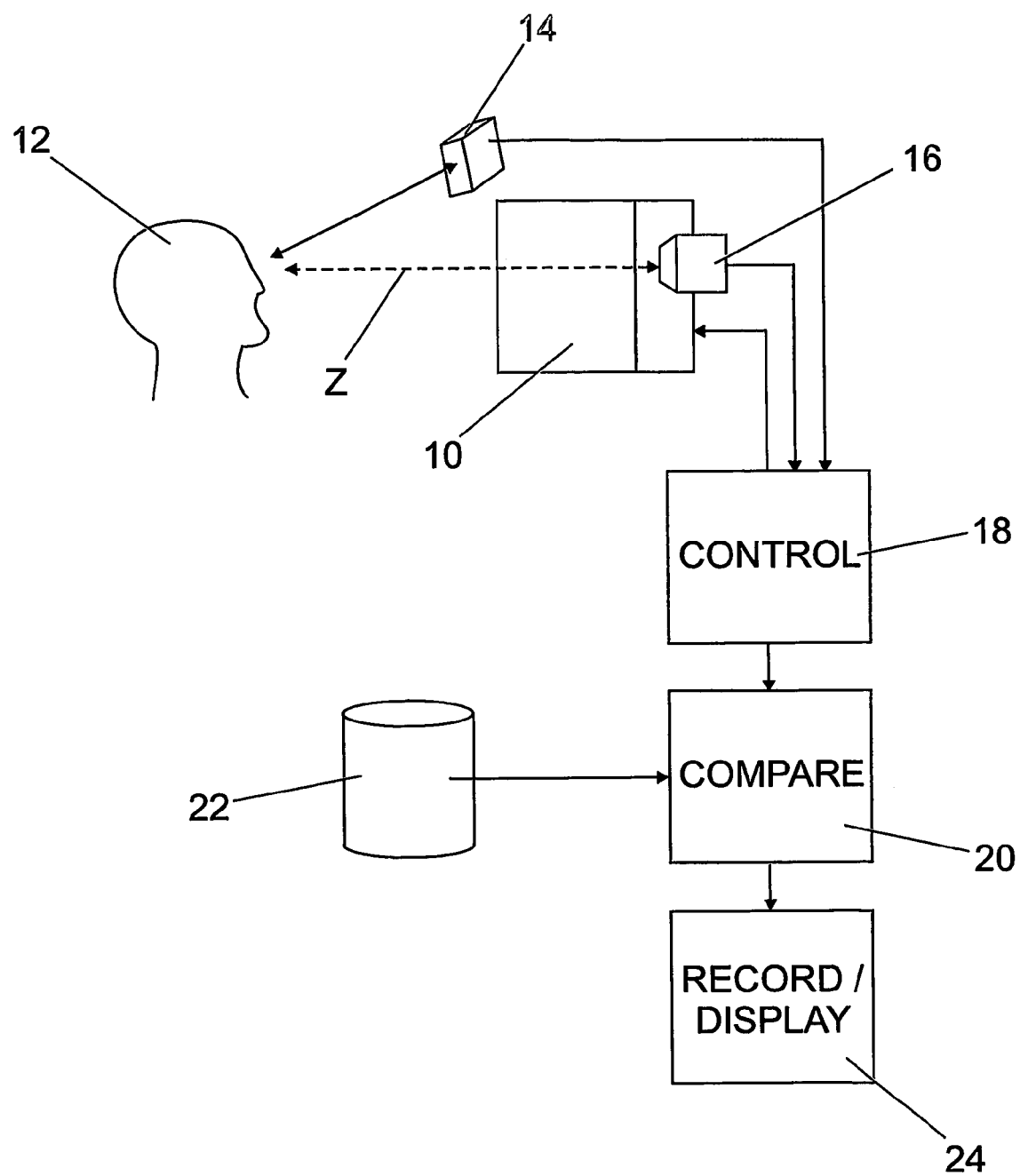

This invention relates to methods and apparatus for assessing eye function. The invention is useful inter alia in the diagnosis of glaucoma and other visual disorders, and in the assessment of dyslexia and neurological conditions which affect eye function.

The common form of glaucoma, as is typical of several other visual disorders, is a progressive disease. Currently the disease can be arrested but not cured. Symptoms include the gradual reduction in the field of view of the affected eye progressing in a characteristic pattern. Due to the nature of the human visual system, victims of the disease do not typically notice this reduction in field of view until the disease has already progressed for several years. Instruments exist which can measure the field of view of a patient but all available instruments suffer from three major problems that limit their utility in making an early diagnosis.

First they are both low in resolution and inaccurate. This low resolution means that the slow progression of the disease at typically 1.8% of the field of view per annum can take several years to be detectable. (See for example "Relative rates of disc and field change examined in eyes at high risk" C Scerra, *Ophthalmology Times* Oct. 15, 2001)

Secondly the existing devices and methods are slow and complex in clinical use and hence expensive in practitioner time. This means that even those practitioners who possess a field of view analysis device cannot economically use it as a routine screening device.

Thirdly the existing instruments are inherently expensive and so are not as widely available as is required for the widespread screening necessary for early diagnosis.

At one time it was thought that measurement of eyeball pressure would provide a method for early diagnosis of glaucoma but this has proved unreliable as the correlation between pressure and glaucoma has proved not to be as high as was originally thought. Instruments for the measurement and mapping of the sensitivity of the human retina known as "visual field analysers" or "Static Auto-perimeters" have hitherto required that the subject perform very unnatural and often uncomfortable eye behaviours such as long periods of attempted fixation on a point. Additionally, hitherto such instruments depended on tests requiring a voluntary response from the subject. The subject is asked to concentrate on a fixation point and report on the presence and position of stimuli presented to their peripheral vision. This process is both slow and prone to inaccuracy. The ability of the subject to accurately fixate is also known to be poor especially over an extended period and so the accuracy of a purely fixation point to stimulus measurement is further compromised.

This invention substantially reduces or eliminates these problems and introduces an entirely novel method and apparatus that allows the subject under test to behave completely naturally (in the sense that they are not required to suppress natural visual reflexes) which both improves accuracy and lowers the stress on the subject. Furthermore the disclosed method and apparatus greatly reduces the time required to map the visual field, which makes the test far more economic and practical for routine screening than the existing equipment that requires lengthy tests under expensive expert supervision.

BACKGROUND TO THE METHOD

While eye to hand co-ordination and reaction is relatively slow and subject to variability and improvement from practice, and eye to voice reaction time is even slower, the reaction time of the eye itself to stimulus is extremely fast in humans and primates. The eye muscles reflexively react to stimuli without the need for conscious action by the subject. Although this reflex can be consciously overridden, the nature of the stimulus and prior fixation can be engineered by methods disclosed in this invention to ensure that the reliability exceeds 97 percent. Furthermore, because the eye reflex is inherently faster than eye-hand or eye-voice reaction times, any variability in the response has a far lower impact on the accuracy of a reaction dependent measurement. This allows the apparatus to exploit the time information in a variety of ways to increase the data obtainable from each individual test point.

The invention, which is defined in the appended claims, is based on the use of an eye position-measuring device capable of measurement of eye position at intervals of less than 45 ms, of which several types are commercially available, in conjunction with a display unit capable of displaying a multiplicity of visual stimuli and capable of accurate calibration of luminance sufficient to exceed the desired accuracy of the desired test. The device is configured to detect the rapid motion of the eye (known as a saccade) towards a new stimulus and to use this saccade to determine the moment the subject's visual reflex responds to the stimulus. Since the subject need not consciously respond to the stimuli the entire field of view measurement process can be automated. By way of example, a set of stimuli can be presented, each stimulus initially below expected threshold increasing in brightness until the stimulus triggers the reflex saccade of the eye from a fixation stimulus. The time the reflex saccade is detected is used to determine the threshold of the retina for that point. The eye position-measuring device can in a preferred embodiment be used to check that the eye's saccade did in fact occur in the correct direction confirming that the test stimulus and not another distraction caused the saccade. At the moment of the said saccade the stimulus that was the saccade target transforms into the fixation point for the next stimulus. This is an important feature for two reasons.

First, the accuracy of immediate post saccade fixation has been shown to be consistently many times better than long term fixation on a single point, and secondly the visual process of saccading from one stimulus to another in sequence is the normal visual scanning mode of the human and higher primate eye, hence the experience for the patient feels natural and unforced, especially if the frequency of the induced saccade is designed to be equivalent to the normal scanning saccade frequency of the eye. This normal scanning frequency varies from time to time in a given individual and from individual to individual but the invention also discloses a method that allows the practitioner to quickly determine this value accurately. Setting the saccade frequency perfectly is not generally necessary but will help to make the test more accurate particularly with anxious patients.

A major advantage of this method of field of view measurement over the prior art is that it eliminates the need for very large samples to be gathered for each stimulus position and repetitive confirmation of the subject's observation of the stimulus and the reliability of their visual fixation. This vastly reduces the time needed for a diagnostician to establish a subject's field of view.

In preferred forms, the invention exploits a detailed computer model of the human visual system's autonomic reflex timings and uses a response interpolator based on this model to allow more accurate interpretation and extrapolation from data while ensuring that the conditions of the test more closely approximate normal visual tasks. This improves both the comfort of the subject and accuracy of the test results. The invention allows sufficient accuracy to determine progression from one test to another of a fraction of a percent, takes little clinical time to administer and the apparatus itself is economic and easily affordable.

In addition to the above benefits the nature of the disclosed method and apparatus also has utility in diagnosis of other visual disorders not directly related to visual field but still dependent on the exploitation of the computer reflex model. This allows the invention to be applied to the diagnosis of high function visual disorders such as dyslexia and visual "neglect". Dyslexia is a higher brain function disorder, which can be improved by appropriate training, and "neglect" is a symptom of a particular form of brain damage.

SUMMARY OF THE INVENTION

The invention provides a method as defined in claim 1, apparatus as defined in claim 24, and also a software package as defined in claim 40.

Preferred features of the invention and benefits thereof will be apparent from the subordinate claims and from the description.

DETAILED DESCRIPTION OF PREFERRED EMBODIMENTS OF THE INVENTION

Figure 2:
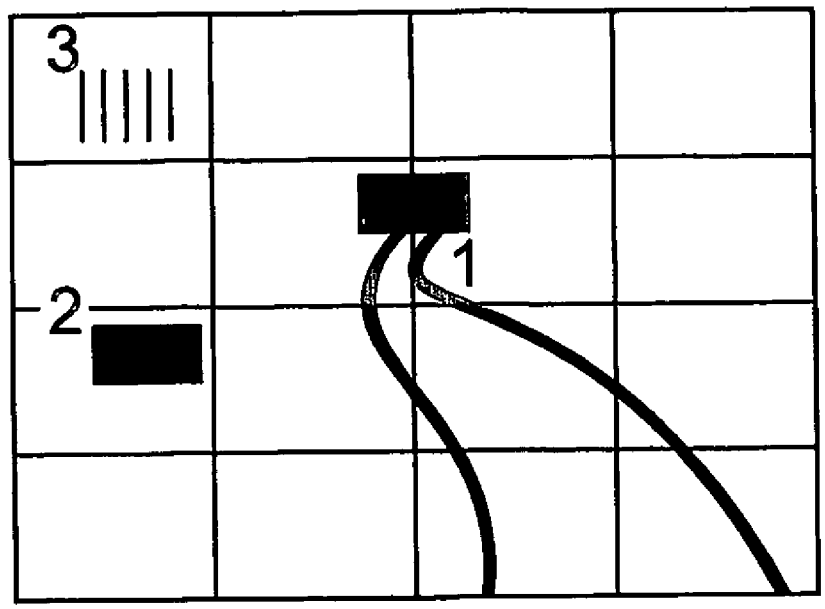
Figure 3:
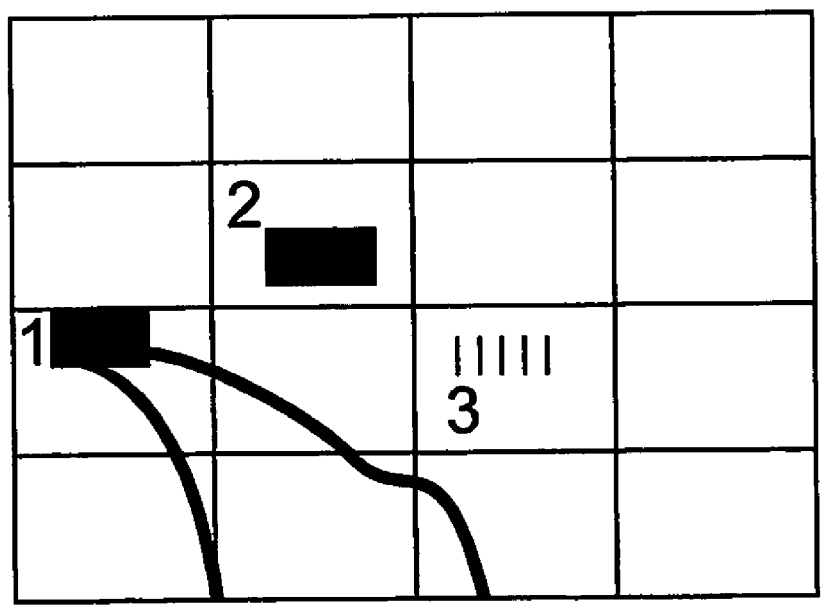

Embodiments of the invention will be described, by way of example only, with reference to the accompanying drawings, in which:

FIG. 1 is a schematic illustration of one apparatus embodying the invention; and FIGS. 2 and 3 represent images used in one method according to the invention.

Prior to this invention visual field analysis methods and apparatus have been extremely crude, in general consisting of an array of lights or other display illuminated under a pseudo-random protocol and at varying brightness straddling the expected threshold of the retina and a fixation point to attempt to maintain some minimal knowledge of the eyes position prior to stimulus. Unfortunately the human vision system is particularly poor at maintaining a constant fixation and furthermore even if this is achieved with practice there are side effects to concentration on a fixation point that significantly reduce the accuracy of the measurement. As a consequence most of these machines are, in practice, little better than the intelligent use of a pen waved at the subject by the practitioner. They provide a rough map of defective areas but the positional accuracy of the defect perimeter is grossly compromised by the impossibility of accurate fixation maintenance by the subject and furthermore the nature of a pursuit or fixed fixation task in itself causes large variations in the subjects' apparent peripheral retinal sensitivity. In research applications with volunteer subjects who are practiced in the use of the instrument these instruments do provide useful data but as a routine diagnostic tool they are simply too complex, time consuming and difficult to use for both the practitioner and the patient.

The following references confirm this assertion:

"Selective Peripheral Fading: Evidence for Inhibitory Effect of Attention on Visual Sensation"

Lianggang Lou

Department of Psychology

The University of Hong Kong

Barbington-Smith B, 1961 "An unexpected effect of attention in peripheral vision" Nature (London) 189 776

Duncan J, 1980 "The locus of interference in the perception of simultaneous stimuli" Psychological Review 87 272-300

The prior art of which the following small sample is typical, ignores the nature of the human visual system as a whole. In the absence of such a model the measured values for a given point in the field of view will be tend to be grossly inaccurate both spatially (topologically) and in amplitude terms. The results are akin to plotting the chart of a shoreline with an elastic plumb line and a faulty sextant.

As stated above the prior art consists primarily of various methods of presenting varying brightness stimuli to the eye from various angles depending on some form of fixed or moving reference fixation point to deliver geometric accuracy or they include some form of eye tracking system which requires a calibration that is itself subject to the same error of fixation as the untracked test. All of the prior art requires significantly abnormal eye behavior from the subject under test over typically tediously long periods. As the above references show such abnormal fixation behavior inherently destroys both the topological and amplitude accuracy of the data being collected to the point where it is accepted in ophthalmic diagnosis that the repeatability of the measurements can not be better than plus minus 5 degrees and plus minus 2.5 dB. Given the progress of common glaucoma at 1.8 percent per annum this means in practice that a confirmed diagnosis of glaucoma can take the several years required to establish the nature of progression with such low repeatability instruments.

EXAMPLES OF THE MOST COMMONLY USED PRIOR ART

U.S. Pat. No. 4,561,738: Field tester

Humphrey; William E., San Leandro, Calif.

Campbell; Charles, Berkeley, Calif.

U.S. Pat. No. 5,050,983: Visual testing method and apparatus

Johnson; Chris A., Davis, Calif.

Shapiro; Lionel R., Davis, Calif.

U.S. Pat. No. 5,024,519: Apparatus and method for visual-field testing

Howard; Dwight L., Winters, Calif.

Johnson; Chris A., Davis, Calif.

The present inventors theorised that if a test method could be devised that allowed the patient to behave as naturally as possible it would consequently be true that the patient's autonomic responses would more reliably follow normal repeatable curves. The inventors also researched both fixation and stimulus methods that promote relaxed natural reflex saccades. By carefully researching the limit and variability of these normal responses it would be practical to gather information about the eye's sensitivity and visual field from careful timing of the natural saccade responses to stimuli. This could be applied to several visual stimuli ranging from a carefully sequenced repetitive single point stimulus similar to a conventional visual field analysis method to the presentation of specially formatted images or video sequences where the saccade timing variation between a normal and a visually impaired individual could be made readily apparent.

This theory was subsequently proved to both the inventors' satisfaction and led to the present invention.

Referring to FIG. 1, one embodiment of apparatus for use in the invention comprises a display screen 10 viewed by a subject 12. Any suitable display may be used which is capable of presenting images where the luminance of any point in the image over the desired field of view can be defined at least as accurately as the desired amplitude accuracy of the desired retinal map. Preferably, the display is capable of presenting an animated fixation image consisting of a substantially stationary central region comprising at least 20 percent of the diameter of the fixation image, and a mobile perimeter defined such that the perimeter is less than 3 degrees of the arc of vision of the subject in diameter. By way of example, such a fixation image might consist of an insect such as a ladybird with wiggling legs acting as the mobile perimeter, or in a more abstract form a central disc with an eccentric ring with the perigee rotating about the central disc.

An eye position sensor 14 detects movement of the subject's eye. The sensor should be capable of measuring eye position at intervals of less than 45 ms. Several types of sensors meeting these requirements are available commercially.

The eye motion sensor typically comprises a video camera connected to a computer, in combination with software executed by the computer. The software compares each new frame of the video output from the camera to an average of a previous plurality of frames, typically two to five video frames depending on required sensitivity and speed of response. The frames are compared in terms of each RGB value for each pixel and a threshold difference is set determining the change in RGB value that constitutes a motion fast enough to be a saccade of the pupil. The averaging of the previous group of frames eliminates noise differences and the threshold determines both the magnitude and speed of a motion in the frame. The video cameras are mounted on a headset and may be wirelessly connected to the computer, suitably via a 1.2 or 2.4 GHz wireless video link. Suitable cameras are available from Ajoka, Swan and Sony. Sony cameras can also be run at very high frame rates and so can improve accuracy. The eyes are preferably illuminated with infra red light so that the image is monochrome whether the camera is colour or not.

A distance sensor 16 monitors the distance between the subject and the display in at least the z-direction (i.e., the direction orthogonal to the left/right and up/down movements of the subject's eye). The distance sensor is preferably one which is non-contact and thus does not restrain head movement, for example ultrasonic ranging, laser ranging, stereo or mono video perspective analysis, suitable forms of which are available commercially. Contact means which do not unduly constrain head movement may also be used but are not preferred.

Typically, the z-measurement is made by an ultrasonic ranging system coupled to the computer (e.g. via RS232), available from Miford Instruments as one example. However, alternative ranging systems could be used. One option is a second video camera mounted on the test screen top center and connected to the computer (e.g. via USB), which detects the pupils of the eyes using an infra red source co-axially mounted with the camera lens via a beam splitter, or simply placed as close to the lens as possible. This produces bright spots at the pupils as seen by the camera (the same effect that causes "red eye" in a flash photograph). The camera image can be adjusted via brightness and contrast and suitable infra red pass filters so that only the pupils are seen in the image as two bright dots. Software determines the distance between the two dots. Suitable software is commercially available but is also easy to write from scratch. One supplier of suitable software, called Common Vision Blox, is Image Labs International, Montana USA, who also produce software components suitable for use in the motion detection previously described. In use, the optician enters the Inter-Pupil Distance to the system and the z-distance can then be calculated from knowledge of the apparent separation of the pupils, the focal length of the lens and the size of the image sensor.

A control means 18 controls the display on the screen 10 and receives and processes data from the sensors 14 and 16, in particular data relating to the timing and direction of saccades following the presentation of stimuli. Comparison means 20 compares this data with a library of information held in a database 22, and results are output to a recording or display means 24. The various elements 18, 20, 22, 24 may suitably be incorporated within a general purpose computer.

Unlike the prior art, the present invention uniquely exploits an accurate model of the autonomic visual reflexes and interrelated aspects of visual perception in humans and higher primates to vastly improve the accuracy and repeatability of the measurement. This model is incorporated in the timing versus illumination increments described in the method. Additionally, the natural interaction of the device with the subject eliminates stress and fatigue in the test that further enhances the repeatability. Uniquely, after rapid basic mapping of the visual field the device allows the detailed plotting of any portion of the retina such as the perimeter of a defect to a repeatable accuracy of a fraction of a degree, allowing defect progression rates of 1 degree per annum or less to be detected and characterised by tests separated by weeks rather than years.

The models of the autonomic visual reflexes and interrelated aspects of visual perception incorporated in the method and apparatus include the property of the human optical system that perceives stimuli of higher intensity earlier than stimuli of lower intensity. This effect is primarily the consequence of the integrating nature of the retina. The longer a given brightness shines on a given area of the retina the more photons are delivered to the integration until eventually the threshold is crossed, the speed of transit of visual stimuli through the nerve and visual cortex to the brain is also varied by the relative intensity. This gives rise to the phenomenon known as the "Pullfrich effect" after the discoverer who described several optical illusions for which the said intensity dependent delay is responsible. It has been used as a method for pseudo stereo image presentation. In the prior art stimuli for visual field analysis have been generally presented for a given fixed time as well as a given brightness so that the threshold of the retina could be determined. This required the sequential and separate presentation of stimuli of different brightness for any given point to establish the threshold of the retina as in U.S. Pat. No. 5,024,519 and others. Such a method is extremely time consuming but hitherto the integration effect precluded the possibility of simply delivering a stimulus of increasing brightness at a given point as there was no way to determine the precise moment that the stimulus was perceived.

Conversely, in the present invention the eye's saccade reflex is modeled in the computer timing so that the moment of perception can be derived from the time interval between the induced saccades. The integration time is exploited to refine the accuracy of the sensitivity measurement of the retina and simultaneously minimize the duration of the test. The equations below demonstrate how this is achieved despite the fact that while the retinal integration is exponential up to the retinal threshold the Pullfrich delay continues to reduce linearly as the stimulus becomes brighter. Hence the time from presentation to the triggering of a saccade will be tens of milliseconds longer for a dimmer stimulus even if both stimuli integrate above the retinal threshold in less than a millisecond. Conversely if the stimuli took 200 ms or more to integrate above threshold the latency delay before the saccade after the retinal threshold is crossed would be much longer than for the previous example so the resulting total delay would be much longer effectively amplifying the time difference between saccades stimulated by different threshold levels of different points on the retina.

In conventional static auto perimetry, stimuli are presented for a fixed time and so deliver a fixed energy to the retina. The patient is asked to press a button or vocalise if they see a given stimulus at a given point while fixating on a central fixation point. Crucially they must suppress any reflex saccade as best they can to any stimulus during the test. This suppression is uncomfortable to achieve and also causes a subconscious distraction that reduces the patient's accuracy on an already difficult task. Most auto perimeters offer two basic types of test. In one type the stimuli are presented at levels which are just below or just above the expected threshold at a given point and the test is repeated for each point in a "staircase" where if the previous stimulus for a given point caused a patient response then the next stimulus would be presented at 2 to 3 times the desired amplitude resolution below the previous stimulus, and so on till the stimulus fails to generate a patient response. Then a further stimulus is presented halfway between the brightness of the last stimulus that caused a response and the stimulus that failed to cause a response. The final threshold value is then set depending on whether or not the patient responds to this stimulus. Obviously if the patent had failed to respond to the first stimulus in the sequence the next stimulus would be brighter rather than dimmer and the overall sequence would be the reverse of the above. Clearly this method takes a long time, as each point in the retina will typically need five stimuli to determine the threshold. Most auto-perimeters offer an alternative so called "supra threshold" test where each point in the retina is presented at an amplitude calculated on the basis of demographic ophthalmic data to be just above the expected threshold for each point thus a basic plot of areas below a chosen threshold can be plotted. This method is relatively crude of course and does not provide any detailed contour data of the threshold sensitivity.

As will be obvious from the above, the stimuli are inherently presented in the above tests at or close to the patient threshold. Since the total energy of the stimulus is critical this means that the stimuli are either very dim or of very short duration. In both cases the patient is required to respond consciously to stimuli that in practice are extremely ambiguous. The patient will constantly be marginally aware of stimuli and be consistently uncertain as to whether or not they "saw" a stimulus. Patients report that this is extremely stressful. Practice improves the patient's confidence and so the reliability of the test but such practice is not practical for a routine diagnostic test. The test is further compromised because it is inherently difficult to fixate on a single point accurately. This has two consequences. Clearly if the fixation point is uncertain, then the positional accuracy of any test point on the retina is equally uncertain; but the problem is made worse by the fact that the eye's small movements around the fixation mean that the total time a given stimulus illuminates a given point on the retina is variable and so the total integrated energy on that point varies far more than is desirable. The above issues are described to clarify the nature of the present invention.

In the present invention the threshold of the retina is determined by the delay between the presentation of a stimulus and the triggering of a reflex saccade to that stimulus. If the stimuli are of low brightness then this time delay will include a period of integration to the point where sufficient energy has been delivered to the retina to pass the threshold and a further delay caused by the Pullfrich effect which makes a brighter stimulus travel faster through the nerve path than a dimmer stimulus. If the stimuli are of higher brightness then the integration time will be shorter and the Pullfrich delay will also be shorter because once the retinal threshold is passed the energy is still integrating on the retina and so the brighter stimulus will travel through the nerve path very much faster. This means that varying the brightness of the stimuli will vary the average time of the saccade response and so the resolution of the amplitude measurement is determined by the resolution of the measured time increment and the chosen brightness. In principle it would be assumed therefore that a dimmer stimuli set would provide a more accurate measure of the retinal amplitude sensitivity as a function of time. While this is true to an extent, the present invention aims to achieve a more accurate spatial plot as well as a more accurate amplitude plot. It is central to this invention that the accuracy of the eye fixation is superior for a few hundred milliseconds post saccade to its accuracy over a longer time therefore the time resolution of the measurement must be balanced against the deteriorating accuracy of the fixation over time. Additionally if the test is delivered close to the normal visual scanning saccade frequency of between 1.2 and 5 saccades per second the test will feel even more comfortable and natural for the patient.

Thus in simplified terms, ignoring the integration loss and limit and the precise function of the Pullfrich delay which will be clarified later, the time T between the commencement of a stimulus point and the resulting saccade of the eye to that stimulus is expressed by the function Eq 1:
$$T = \frac{(t^2 \cdot l + P)}{(t \cdot l)}$$

where t is the total time for the luminance "l" to integrate to the detection threshold of the retina and P is the Pullfrich delay for an arbitrarily chosen luminance "h" where $h = t \cdot l$.

t can be derived from the function:

Eq 2:
$$\begin{bmatrix} \frac{-l}{(2 \cdot l)} \cdot \left(-T \cdot l + \sqrt{T^2 \cdot l^2 - 4 \cdot l \cdot P}\right) \\ \frac{-l}{(2 \cdot l)} \cdot \left(-T \cdot l - \sqrt{T^2 \cdot l^2 - 4 \cdot l \cdot P}\right) \end{bmatrix} = t$$

Naturally the greater of the two solutions is the true result since clearly the arbitrarily chosen luminance is chosen to be greater than "l". Hence for any given level of light used as a stimulus the integration time t to h can be determined from the total time T. This means that relative sensitivity of the retina from one point to another is expressed directly as a function of t and can be derived from the interval time T and the resolution of the measure can be adjusted by increasing "l". The overall speed of the test and the average time between saccades can be adjusted for maximum comfort and accuracy by adjusting l to meet the criterion of average saccade time of between 200 and 800 ms described above.

The resulting value of t can be used directly to plot a relative sensitivity map of the retina. However, often it will be required to translate these relative values to commonly used units of measure of the retinal threshold sensitivity. In that case the functions of the retinal integration and the true function of the Pullfrich delay become important. A useful optional feature of the invention is that the stimulus can be increased or decreased in brightness from its initial presentation brightness, such an increase or decrease can be used to modify the function of T to t to make the resulting function either more or less linear as desired. Clearly in the absence of this feature the dynamic range of the test would be limited if the time intervals are limited as required to maintain a natural rhythm. Increasing the stimulus brightness during presentation is of particular use in the testing of a subject with known defects since the stimuli can be rapidly increased in brightness once a predetermined threshold is passed, thus speeding up the test on a subject who would otherwise register a large number of missed stimuli or take so long for each stimulus that the natural comfort rhythm is broken.

The retinal integration function is quite complex as discussed by T E Cohn of Berkeley in his paper "Integration by the human eye; implications for warning signal design". In the typical embodiment of the invention the retinal integration to threshold can be taken as above which follows the standard Bloch's Law which states that the product of intensity of a brief flash of light times the time it is on is a constant at threshold. Beyond Bloch's integrating time, usually taken as 0.1 sec, threshold declines only modestly as duration increases until, for long durations, threshold is a constant. This can be enhanced by a simple two-limbed approximation to this threshold function which obeys Bloch's law for short durations and obeys the relation that threshold is constant for longer durations. This is The Blondel-Rey law. It is a simple way of summarising this two-limbed function. It states that the product of a flash intensity times its duration is equal to the asymptotic threshold value times the sum of the duration plus a visual response time constant described above.

In certain embodiments of the invention where longer time intervals are desired it may be considered worthwhile to improve the accuracy of the system by utilising the more accurate Blondel-Rey law, however the error induced by the use of the less accurate Bloch's Law at the ideal timing intervals recommended for the method are in practice less than errors due to the reflex variables in the eye and so, while the overall error budget can be reduced by the use of the most accurate integration formula, the accuracy of the Bloch Law embodiment is still substantially better than that achievable by the staircase method in conventional auto perimetry.

The Pullfrich function is essentially linear provided the stimuli are of sufficient brightness to exceed threshold in less than 400 ms, so again the best performance of the system will be achieved at or close to the natural saccade rhythm of the eye in scanning mode. This natural rhythm has been determined by the inventors in a study of over 150 individuals to approximate, to within 20 ms, a value defined as the subject's "natural counting rhythm". It is well known that people tend to count much faster than once per second and so various word delays are recommended to lengthen the counting rhythm to approximate a second more accurately when people desire to time an event without a watch. The inventors speculated that the natural rhythm would inherently be proportional to the subject's conscious reaction time. It proved to be that a person's expressed maximum comfort zone in terms of saccade frequency exactly matched the subject's natural counting frequency to within 20 ms. This proved to be true despite a variation of well over a factor of two in different individuals' natural counting rhythm and also to a similar variation for a given individual in different states of fatigue or arousal. This fact can be used by a practitioner using the invention to set the ideal brightness of the basic illumination level of the stimulus by asking the patient to count up to ten or count aloud the number of items on a screen presentation. The faster the patient counts the brighter the basic stimulus should be for maximum comfort in the test. Alternatively the practitioner can use the count test to determine the patient's level of anxiety and arousal and may take steps to calm the patient until they demonstrate a slower count rhythm and so allow a slower and therefore higher resolution test.

It should be clear from the above that the accuracy of the test can be enhanced by repeating the test with different basic illumination levels, since the threshold value for a given point and the integration time should correlate exactly. In general, however, it would not be necessary to repeat the entire test; rather the test points for any anomalous areas can be tested again at a different brightness and the integration time measured for that brightness can be correlated with the original data. If the two values agree then the value is certain: if they disagree a further test at either of the two previous brightness levels or alternatively at a third brightness level can be applied. If this third test yields anomalous results then the data should be discarded for that point but in practice this occurs in less than one percent of the test points.

A modified sequence of test stimuli can be presented to create very high spatial resolution plots of a defect perimeter. This is achieved by presenting a sequence of stimuli in a line crossing the perimeter defect alternating with randomly placed stimuli elsewhere to prevent the patient recognising the pattern. In a preferred embodiment at least some of the alternate stimuli are placed to plot a line to cross other suspected defect perimeter zones. In this latter case there should be at least four plot zones randomly sequenced or, if less than three suspect zones exist, then one or more random stimuli should be presented. It should be noted that such a line of fractional degree difference plot points would be impossible with a conventional central fixation perimeter since the spatial pattern of the plot points would be immediately apparent to the patient. Conversely in the present invention each stimulus that generated a saccade becomes the new fixation point. Combined with the alternating random or alternate zone stimuli this makes the overall spatial pattern perceived by the subject entirely random and unpredictable because, although the stimuli are indeed occurring repeatedly on similar points on the retina, the overall spatial position of the stimuli as perceived by the subject is not repeating.

In recent years an alternative to basic static automated perimetry has been the frequency-doubling test. One example of this method uses a stimulus that consists of light and dark bars of a low spatial frequency (0.25 cycle/degree), flickering in counter phase at a high temporal frequency (25

Hz). Briefly, the flickering produces an illusion of doubling the spatial frequency of the stimulus. The contrast of the stimulus is gradually increased and the examined subject has to indicate when a movement is perceived anywhere in the visual field. The method is assumed to measure the integrity of a particular subgroup of retinal ganglion cell, sensitive to motion. This type of stimulus can be used with the disclosed saccade trigger in a sequence as described for the point stimulus above where the stimulus changes to the fixation point with each saccade. In this case again the absolute threshold function for the contrast of the bars will correlate to the time T as above and hence the range of contrast needed for each presentation of the frequency doubling stimulus target can be reduced, because the stimulus need not initially be presented below the contrast threshold since the time for the saccade to the stimulus will indicate the relative level above threshold of the contrast.

In a further embodiment of the invention the relationship between the comfort frequency of the scanning saccade and the normal human visual search saccade frequency can be used to determine if an individual has defects in the retina by presenting each eye individually with pictures based on principles laid out in detail below. These pictures can be natural images or computer generated images with selected regions of high and low spatial frequency in addition to certain visual cues that the inventors have defined which allow the priority of a typical initial search saccade sequence to be reliably predicted. Because in these special images the initial gaze direction of the eye can be predicted with a high reliability, and at least the first saccade from that initial gaze fixation can also be predicted, it means that in viewing these images the presence of a high spatial frequency feature on the image will cause the eye to be attracted to it after the initial high priority cue subsequent to the primary gaze fixation. In the normal eye only the blind spot exists as an area that obscures a feature that is revealed to the eye when this initial saccade occurs. If an area of high spatial frequency is revealed as the blind spot moves this causes a change in both the saccade priority AND causes the natural scanning rhythm to "reset" to initial search mode. Since the initial search saccade frequency is much more rapid than the natural scanning frequency, any region of high spatial frequency or other high priority cue revealed as the eye initially saccades causing a defect to cease to obscure the said cue will cause a second burst of high frequency saccades as the eye attempts to accommodate for its lack of expected peripheral vision definition by scanning the revealed cues with the fovea. This is an especially useful test since it detects even quite shallow anomalies in the eye even if the contrast differential of the image is much higher than the anomaly depth. The images are designed to cause scanning saccades of relatively small amplitude but the presence of an anomaly will cause a large amplitude saccade as the fovea moves to accommodate as described above, and hence both the frequency of the saccades and the amplitude can be used to signal the presence of an anomaly. In this case time from the initial saccade to the triggered saccade is inversely proportional to the depth of the saccade because the differential between the anomaly and the normal portion of the retina is equivalent in practice to the contrast or differential above threshold described for the previous tests in terms of the relationship between stimulus and the speed of the saccade reflex. The location of the saccade spatial frequency cues can be set in a sequence of images to digitally sequence the areas of interest on the retina. For example eight images presented in sequence can detect the presence of an anomaly one $64^{th}$ of the visual field for each eighth of the visual field tested in each image. Theoretically this could be further refined by further subdivision but in practice it is probably better to revert to either frequency doubling or constant stimulus plotting if detailed plotting is desired. This image test is best used as an "instant" detector of the presence or absence of anomalies worthy of more detailed diagnosis.

Depending on the desire of the practitioner the image colours can be chosen to cover either the full spectrum or selected colours such as blue and yellow that preferentially shows cone anomalies and is therefore more sensitive to relatively small pathologies of the eye.

The basic rules of the image design for predicted priority sequence are as follows:

A solid perspective cue such as road, path or river with a dark end point will draw the first gaze fixation. This will be followed immediately by a saccade to the darkest area of the image coupled with any high spatial frequency data followed by a saccade to the next highest spatial frequency region that is also dark or to the highest spatial frequency area of any brightness if there are no more apparently dark areas of the image. These cues should be set at least ten degrees apart. In a normal vision subject these initial three saccades will occur in less than 400 ms followed by much slower "count" frequency saccades of less than 10 degrees amplitude as the eye assumes normal scanning mode. If however any area of the eye has a defect that uncovers an area of high spatial frequency then the image effectively re-triggers the eye/brain system to repeat the initial search sequence and so the high frequency high amplitude saccades will continue for at least twice the duration of a normal vision subject.

FIGS. 2 and 3 show representative figures as an example to clarify the principles of the images. Note that the real images may be computer generated photo realistic images or abstract images. The critical aspect is that they follow the principles laid out here.

In FIG. 2, the first fixation is marked as 1 the dark area at the end of the "perspective suggesting" path. The area of the retina effectively under test is 3 and the second fixation attractor is 2. In a normal vision subject the spatial frequency attractor at 3 does not change during the saccade from 1 to 2 and so does not cause an immediate saccade whereas if a defective area of the retina obscured the high spatial frequency attractor at 3 when fixating on 1 then it would "appear" to the eye immediately after the saccade to 2 and so trigger a reflex saccade. It should be noted that should the subject in fact saccade instead to 3 instead of 2 after 1, this obviously by definition demonstrates that 3 was not under a region of low sensitivity or resolution. This means that this type of test is uniquely free from false positive results which is a great advantage in any screening diagnostic test.

FIG. 3 illustrates the test being repeated for a subsequent field.

A sequence of images covering the entire field sector by sector can be presented to the patient. The high spatial frequency sector should be no greater than 0.25 degrees per cycle for the areas outside the central ten degrees from the fovea. Ideally the high spatial frequency sector should be more than twice the average spatial frequency of the rest of the image and regions less than half the average spatial frequency should be avoided, as this can tend to alter the saccade priority from the ideal.

It should be noted that although the term "perspective" is used this is not intended to mean necessarily true perspective image. The human vision system is so tuned to seek perspective cues that any apparent taper however distorted will tend to be read as a perspective cue. This has been shown in our research to be almost always the primary cue in an image since the brain seeks a sense of scale in any image with an extremely high priority. However areas that suggest shadows or doorways that may obscure potential threats are very high priority too. This proved to be so even with very young subjects; the inventors suspect this is a fundamental survival trait that is as genetically programmed as the blink reflex is to an apparent direct threat to the eye. The combination of a "suggested perspective" cue and a dark "doorway" cue is virtually 100 percent reliable as a trigger of the first gaze fixation. In fact no subject in the test trials ever failed to fixate first on such a cue. Note that since the eye saccades to that first cue from its previous rest position no feature of the image is processed by the brain until after the primary gaze fixation.

There are many other cues that the inventors have researched that can be arranged in suitable priority sequences to lend further variety to the test but the above listed are adequate to create a successful visual field defect diagnostic tool as disclosed herein.

It should be obvious that instead of a sequence of still images a moving image of many frames per second could be used provided the said moving image could be divided into two or three second sequences where the saccade priorities of each such sequence were known as above. In such a moving image method stimuli that may cause the eye to enter pursuit mode should be avoided.

In an alternative method a moving image sequence can be used which is designed to exploit the pursuit mode. In that case the pursuit stimulus should be considered the primary fixation. Wherever the pursuit stimulus comes to rest on the screen can be defined for the still images above. In this case the timing period used to discriminate considered as the primary gaze fixation with the second and third priority cues as normal from abnormal eye behavior should be 2 to 3 second sequences free of the said pursuit stimuli.

The apparatus may also be used to test for dyslexia using the Fischer method of determining whether and how well the patient is capable of reverse saccades where the patient is instructed to saccade in a direction OPPOSITE to the stimulus. In this invention the method of the test is a presentation of an image of for example the surface of a rabbit warren. The patient is told that a dot will appear just before a rabbit appears exactly opposite from a moving fixation point and they must identify the rabbit from a group of three recognisable "bunnies". The fixation point is for example a bird or fox image moving across the screen at any angle. A red or other colour bright dot appears at some point and within 50 ms a rabbit appears for 100 to 150 ms exactly opposite to the dot as measured through the fixation stimulus. Normal subjects will in the majority of cases register one saccade whereas dyslexics will in general register two, one for an aborted saccade to the initial stimulus they are told NOT to look at and one for the correction to the rabbit. This is because the ability of the cognitive system to override the reflex to saccade to any stimulus has proven to be consistent with the absence of dyslexia whereas the inability to override has proved to be an indication of the opposite. In this invention the proposed "recognition of the rabbit task" or similar recognition task is a strong incentive to saccade as early as possible to see the "rabbit" long enough to recognise it. It is critical to the invention that the features of the rabbit or other recognition task that differentiate it from the other samples previously shown with it to the subject must be of such fine detail as to only be visible to the fovea. If the person waits till the "rabbit" appears before saccading then the saccade will arrive too late for the brain to have time to image the rabbit adequately for recognition. Hence simply suppressing the reflex response to the red dot stimulus is not a solution to the task only if the subject saccades opposite to the stimulus will the subject be looking at the point where the rabbit appears and so get enough time with the rabbit imaging on the fovea to allow recognition. This requires that the eye is capable of saccading at near reflex speed in the opposite direction to the stimulus. This task is possible at about 75 to 90 percent of the time for a normal individual above the age of five. It is impossible for children aged three or less and it is virtually impossible for even mild dyslexics. For example the set of rabbits in the test might be drawn with one two or three sets of whiskers with an apparent diameter of 0.1 to 0.3 degrees. In such a case only the fovea would have sufficient resolution to perceive the whiskers well enough to count them.

In a further embodiment of the invention, means are provided to illuminate the eye preferably in the infra red region capable of creating a clear highlight on the cornea as viewed by a camera and means whereby the camera delivers images in an electronically interpretable way to a calculating device such that the highlight reflections of the cornea of both motion blurred and non blurred images may be analyzed by commercially available software algorithms to determine the angular moment of the blur which in turn defines the direction of the eye's movement causing the motion blur. Such means are used to interpret the saccade results to confirm that the saccades were induced by the stimulus and not other distraction.

The test data can also be compared with a library of data categorised for factors including age that affect the normal sensitivity of the retina and a second database of diseased and other abnormal retinal data that may be compared to the measured retinal data with a view to allowing a software algorithm to suggest a possible diagnosis based on said similarity by means of superposition of perimeter and sensitivity data for each defect on images of perimeters stored in the database of diseased and other abnormal retinal data.

This can be done by assessing geometric similarity to a set of images where the set contains a majority of data from a given disease or other abnormal category would trigger the algorithm to suggest the majority disease as the probable diagnosis, such majorities being passed to a second database on confirmation of the said diagnosis over time. This second database is a refined rapid search evolved version of the first database that may be used preferably to the first when it exceeds a sample size of at least 4 times the average majority sample size.

Improvements and modifications may be incorporated without departing from the scope of the invention as defined in the claims appended hereto.

The invention claimed is:

1. A method of assessing eye function, comprising:
   (a) providing an image area in which images can be presented to the eye, and in which the luminance of any point in the image area over the desired field of view under test can be defined at least as accurately as the desired accuracy of a retinal map to be obtained;
   (b) forming a fixation image;
   (c) presenting a stimulus to the eye at a location within the image area spaced from the fixation image;
   (d) detecting a saccade triggered by said stimulus and immediately removing the original fixation image and creating a new fixation image at said location;
   (e) recording the timing and magnitude of the saccade and the subsequent fixation;
   (f) repeating steps (c) to (e), and (g) comparing the results with a database of typical eye responses, wherein each of the fixation images is an animated fixation image comprising a substantially stationary central region comprising at least 20% of the fixation image and a mobile perimeter defined such that the perimeter is greater than 3% of the arc of vision of the test subject in diameter.

2. The method of claim 1, further including determining the location of the subject's head relative to the image in at least the z-axis, without applying any constraint to the head motion.

3. The method of claim 1, including the step of calculating the time T between the commencement of a stimulus point and the resulting saccade of the eye to said stimulus expressed by the function Eq 1:
$$T = \frac{(t^2 \cdot l + P)}{(t \cdot l)}$$

where t is the total time for the luminance "l" to integrate to the detection threshold of the retina and P is the Pullfrich delay for an arbitrarily chosen luminance "h" where h=t·1.

4. The method of claim 3, in which t is derived from the function:

Eq 2:
$$\begin{bmatrix} \frac{-l}{(2 \cdot l)} \cdot (-T \cdot l + \sqrt{T^2 \cdot l^2 - 4 \cdot l \cdot P}) \\ \frac{-l}{(2 \cdot l)} \cdot (-T \cdot l - \sqrt{T^2 \cdot l^2 - 4 \cdot l \cdot P}) \end{bmatrix} = t.$$

5. The method of claim 4, in which a software algorithm is used to solve Equation 2 and use the greater of the two results as the total amplified value sensitivity of a given retinal point whereby relative sensitivity of the retina from one point to another is expressed directly as a function of t and can be derived by the software from the interval time T.

6. The method claim 3, in which the intensity of "l" is adjusted to vary the resolution of the measurement.

7. The method of claim 6, in which "l" is adjusted to give an average saccade time of between 200 and 800 ms for maximum comfort and accuracy.

8. The method of claim 3, in which the resulting value of "t" is used directly to plot a relative sensitivity map of the retina.

9. The method of claim 3, in which a software algorithm is provided to translate the relative values of T to commonly used units of measure of the retinal threshold sensitivity by look up table or direct function based on the Blondel-Rey law or Bloch's law.

10. The method of claim 3, in which the stimulus can be increased or decreased in brightness from its initial presentation brightness during presentation, such an increase or decrease being used to modify the function of T to t to make the resulting function either more or less linear whereby to maintain the overall test speed at a rate most comfortable to the patient.

11. The method of claim 3, in which several images are simultaneously presented of a resolution of less than 0.3 degrees only resolvable by the fovea, such that the eye is induced to sequentially saccade at the natural saccade frequency of the patient's natural visual scanning mode.

12. The method of claim 11, in which the value of "l" is selected to induce a saccade frequency close to the said natural scanning mode.

13. The method of claim 1, in which a sequence of visual stimuli is presented in said image area in a random or pseudo random sequence such that the position and preferably the expected time of appearance of the next stimulus in a sequence is not readily apparent to a person viewing the display.

14. The method of claim 3, in which the timing information is compared to a database of timings for a population of humans of various ages such that the integrated timings of T can be compared to an average population of the same age as the patient under test such that the said value of T can be assigned the value of zero.

15. The method of claim 14, in which the timing information is compared with a further model of the relative normal values of integral T over the full area of the retina such that the normal variations of the retinal sensitivity with respect to angle from fovea may be corrected to zero such that any deviation from, the norm will be represented as positive or negative values relative to the normal value.

16. The method of a claim 1, in which there are displayed images containing a known priority sequence of predictable fixation points at separations of greater than 10 degrees of approximately half or less the average brightness of the image and where at least one region contains a further sub-image of a recognizable structure or alphanumeric character or pictorial representation of an object with a resolution of approximately 0.25 degrees per cycle; and in which an alarm or notification is delivered when more than one sequence of saccades of sub 100 ms and greater than 10 degrees occurs per overall image and records the overall time of the sequence of sub 100 mS saccades.

17. The method of claim 16, in which said image is a cartoon character, an animal picture, a vehicle, or a personality.

18. The method of claim 16, in which the threshold of 100 mS is varied to accommodate intoxicated, brain-damaged or other abnormal patients based on an average timing of a sequence of single region of interest images as the norm for a given intoxication, brain impairment or other abnormality.

19. The method of claim 16, in which the images are part of a video or moving film sequence.

20. The method of claim 19, in which the initial fixation cue comprises the termination of motion of an image that induces the eye pursuit of said image.

21. The method of claim 1, in which the image contains a moving stimulus traveling across the display and where a sub-image of high detail only capable of discrimination by the fovea is presented for a period adjustable between 100-600 mS within a given time of the presentation of a simple bright stimulus on the opposite point of an axis drawn through the moving stimulus, said given time being shorter than the time required by the subject to saccade to the simple stimulus and back to the complex stimulus, preferably 50 ms.

22. The method of claim 1, in which the first fixation image is formed by a dark area to which the eye is drawn by an image area giving an impression of perspective, and in which at least the first stimulus is formed by an image area of high spatial frequency.

23. Apparatus for use in assessing eye function, comprising:
   (a) display means for presenting images to the eye where the luminance of any point in the image over the desired field of view under test can be defined at least as accurately as the desired accuracy of a retinal map to be obtained;
   (b) means for generating on the display means an initial fixation image;
   (c) means for generating a stimulus on the display means at a location spaced from the fixation image;

(d) means for detecting a saccade triggered by said stimulus and immediately removing the initial fixation image and creating a new fixation image at said location; (e) means for recording the timing and magnitude of each saccade and subsequent fixation and for comparing the results with a database of typical eye responses, wherein each of the initial and subsequent fixation images is an animated image comprising a substantially stationary central region comprising at least 20% of the fixation image and a mobile perimeter defined such that the perimeter is greater than 3% of the arc of vision of the test subject in diameter.

24. Apparatus according to claim 23, further including means for determining the location of the subject's head relative to the image in at least the z-axis, without applying any constraint to the head motion.

25. Apparatus according to claim 23, including calculating means for calculating the time T between the commencement of a stimulus point and the resulting saccade of the eye to said stimulus expressed by the function Eq 1:
$$T = \frac{(t^2 \cdot l + P)}{(t \cdot l)}$$

where t is the total time for the luminance "l" to integrate to the detection threshold of the retina and P is the Pullfrich delay for an arbitrarily chosen luminance "h" where h=t ·1.

26. Apparatus according to claim 25, in which the calculating means operates to derive t from the function:

Eq 2:
$$\left[ \begin{array}{c} \frac{-l}{(2 \cdot l)} \cdot \left(-T \cdot l + \sqrt{T^2 \cdot l^2 - 4 \cdot l \cdot P}\right) \\ \frac{-l}{(2 \cdot l)} \cdot \left(-T \cdot l - \sqrt{T^2 \cdot l^2 - 4 \cdot l \cdot P}\right) \end{array} \right] = t.$$

27. The apparatus of claim 26, in which a software algorithm is used to solve Equation 2 and use the greater of the two results as the total amplified value sensitivity of a given retinal point whereby relative sensitivity of the retina from one point to another is expressed directly as a function of t and can be derived by the software from the interval time T.

28. Apparatus according to claim 25, including means for adjusting the intensity of "l" to vary the resolution of the measurement.

29. Apparatus according to claim 28, in which "l" is adjusted to give an average saccade time of between 200 and 800 ms for maximum comfort and accuracy.

30. Apparatus according to claim 25, including means for plotting a relative sensitivity map of the retina directly from the resulting value of "t".

31. Apparatus according to claim 25, in which a software algorithm is provided to translate the relative values of T to commonly used units of measure of the retinal threshold sensitivity by look up table or direct function based on the Blondel-Rey law or Bloch's law.

32. Apparatus according to claim 25, in which the means for generating a stimulus is arranged to increase or decrease the brightness of the stimulus from its initial presentation brightness during presentation, such an increase or decrease being used to modify the function of T to t to make the resulting function either more or less linear whereby to maintain the overall test speed at a rate most comfortable to the patient.

33. Apparatus according to claim 23, in which the image display means is adapted to display several images are simultaneously of a resolution of less than 0.3 degrees only resolvable by the fovea, such that the eye is induced to sequentially saccade at the natural saccade frequency of the patient's natural visual scanning mode.

34. Apparatus according to claim 23, in which the stimulus generating means is arranged to present a sequence of visual stimuli in said image area in a random or pseudo random sequence such that the position and preferably the expected time of appearance of the next stimulus in a sequence is not readily apparent to a person viewing the display.

35. Apparatus according to claim 25, including a database of timings for a population of humans of various ages, and including means for comparing measured timing information with the database such that the integrated timings of T can be compared to an average population of the same age as the patient under test such that the said value of T can be assigned the value of zero.

36. Apparatus according to claim 35, in which the timing information is compared with a further model of the relative normal values of integral T over the full area of the retina such that the normal variations of the retinal sensitivity with respect to angle from fovea may be corrected to zero such that any deviation from the norm will be represented as positive or negative values relative to the normal value.

37. Apparatus according to claim 23, in which the image display means is operative to display images containing a known priority sequence of predictable fixation points at separations of greater than 10 degrees of approximately half or less the average brightness of the image and where at least one region contains a further sub-image of a recognizable structure or alphanumeric character or pictorial representation of an object with a resolution of approximately 0.25 degrees per cycle; and in which an alarm or notification is delivered when more than one sequence of saccades of sub 100 ms and greater than 10 degrees occurs per overall image and records the overall time of the sequence of sub 100 ms saccades.

38. Apparatus according to claim 37, in which the threshold of 100 mS is varied to accommodate intoxicated, brain-damaged or other abnormal patients based on an average timing of a sequence of single region of interest images as the norm for a given intoxication, brain impairment or other abnormality.

39. Apparatus according to claim 23, in which the image display means is operative to display an image which contains a moving stimulus traveling across the display and where a sub-image of high detail only capable of discrimination by the fovea is presented for a period adjustable between 100-600mS within a given time of the presentation of a simple bright stimulus on the opposite point of an axis drawn through the moving stimulus, said given time being shorter than the time required by the subject to saccade to the simple stimulus and back to the complex stimulus, preferably 50 ms.

40. Apparatus according to claim 23, in which the first fixation image is formed by a dark area to which the eye is drawn by an image area giving an impression of perspective, and in which at least the first stimulus is formed by an image area of high spatial frequency.

41. A software package containing data enabling the essential timing, control and display mechanisms for carrying out the method of claim 1 using commercially available display, camera and measurement devices.

* * * * *